US010195173B2

(12) United States Patent
Woolf et al.

(10) Patent No.: US 10,195,173 B2
(45) Date of Patent: Feb. 5, 2019

(54) METHODS TO TREAT NEURODEGENERATIVE DISEASES

(71) Applicants: The General Hospital Corporation, Boston, MA (US); Children's Medical Center Corporation, Boston, MA (US); President and Fellows of Harvard College, Cambridge, MA (US)

(72) Inventors: Clifford J. Woolf, Newton, MA (US); Brian Wainger, Brookline, MA (US); Evangelos Kiskinis, Boston, MA (US); Kevin Eggan, Boston, MA (US)

(73) Assignees: Children's Medical Center Corporation, Boston, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/346,478

(22) Filed: Nov. 8, 2016

(65) Prior Publication Data
US 2017/0273930 A1    Sep. 28, 2017

Related U.S. Application Data

(63) Continuation of application No. 14/420,245, filed as application No. PCT/US2013/053766 on Aug. 6, 2013, now Pat. No. 9,517,223.

(60) Provisional application No. 61/680,662, filed on Aug. 7, 2012, provisional application No. 61/791,055, filed on Mar. 15, 2013.

(51) Int. Cl.
| *A61K 31/325* | (2006.01) |
| *G01N 33/483* | (2006.01) |
| *A61K 31/196* | (2006.01) |
| *A61K 31/549* | (2006.01) |
| *G01N 33/50* | (2006.01) |
| *A61K 31/506* | (2006.01) |
| *A61K 31/4409* | (2006.01) |
| *A61K 45/06* | (2006.01) |
| *A61K 31/44* | (2006.01) |
| *A61K 31/27* | (2006.01) |
| *A61K 31/428* | (2006.01) |
| *A61K 31/455* | (2006.01) |

(52) U.S. Cl.
CPC .......... *A61K 31/325* (2013.01); *A61K 31/196* (2013.01); *A61K 31/27* (2013.01); *A61K 31/428* (2013.01); *A61K 31/44* (2013.01); *A61K 31/4409* (2013.01); *A61K 31/455* (2013.01); *A61K 31/506* (2013.01); *A61K 31/549* (2013.01); *A61K 45/06* (2013.01); *G01N 33/4836* (2013.01); *G01N 33/502* (2013.01); *G01N 33/5058* (2013.01); *G01N 2500/10* (2013.01)

(58) Field of Classification Search
None
See application file for complete search history.

(56) References Cited

U.S. PATENT DOCUMENTS

| 5,236,940 A | 8/1993 | Audiau et al. |
| 5,527,814 A | 6/1996 | Louvel |
| 5,849,789 A * | 12/1998 | Rostock ................. A61K 31/27 514/485 |
| 2010/0152116 A1 | 6/2010 | Carmellet |

FOREIGN PATENT DOCUMENTS

| JP | 2002-142610 | 5/2002 |
| JP | 2009-046459 | 3/2009 |
| WO | 1997/15300 | 5/1997 |
| WO | 2005/039577 | 5/2005 |

OTHER PUBLICATIONS

Bock et al., "Reference Maps of Human ES and iPS Cell Variation Enable High-Throughput Charcterization of Pluripotent Cell Lines," Cell, 144:439-452 (Feb. 2011).
Boerio et al., "Excitability Properties of Mouse Motor Axons in the Mutant SOD1$^{G93A}$ Model of Amyotrophic Lateral Sclerosis," Muscle Nerve, 41:774-784 (2010).
Bostock et al., "Axonal ion channel dysfunction in amyotrophic lateral sclerosis," Brain, 118:217-225 (1995).
International Search Report and Written Opinion issued in PCT/US2013/053766 dated Nov. 26, 2013 (12 pages).
Kanai et al., "Motor axonal excitability properties are strong predictors for survival in amyotrophic lateral sclerosis," J. Neurol. Neurosurg. Psychiatry (2012) downloaded at doi:10.1136/jnnp-2011-301782.
Marchetto et al., "Non-cell autonomous effect of human SOD1(G37R) astrocytes on motor neurons derived from human embryonic stem cells," Cell Stem Cell, 3:649-657 (2008).
Rubin, L., "Stem cells and drug discovery: The beginning of a new era?" Cell, 132:549-552 (2008).
Saxena and Caroni, "Selective Neuronal Vulnerability in Neurodegenerative Diseases: from Stressor Thresholds to Degeneration," Neuron, 71:36-48 (2011).
Shibuya et al., "Markedly reduced axonal potassium channel expression in human sporadic amyotrophic lateral sclerosis: An immunohistochemical study," Experimental Neurology, 232(2):149-153 (2011).
Vucic and Kiernan, "Axonal excitability properties in amyotrophic lateral sclerosis," Clinical Neurophysiology, 117:1458-1466 (2006).
Vucic and Kiernan, "Upregulation of persistent sodium conductances in familial ALS," J. Neuronal Neurosurg. Psychiatry, 81:222-227 (2010).
Supplemental European Search Report in EP13827511 dated Feb. 2, 2016 (9 pages).

(Continued)

*Primary Examiner* — Kristin A Vajda
(74) *Attorney, Agent, or Firm* — Fish & Richardson P.C.

(57) ABSTRACT

The specification provides compositions and methods to treat neurodegenerative diseases.

11 Claims, 12 Drawing Sheets

(56) References Cited

OTHER PUBLICATIONS

Wong et al., "Clinical utility, safety, and tolerability of ezagabine (retigabine) in the treatment of epilepsy", Drug, Healthcare and Patient Safety, 2012:4 81-86.
European Communication pursuant to Article 94(3) EPC for Application No. 13 827 511.0-1466 on Jul. 7, 2016, (7 pages).
European Communication in Application No. 13 827 511, dated May 30, 2018, 4 pages.
Zarei et al., "A comprehensive review of amyotrophic lateral sclerosis," Surg Neurol Int, Nov. 2015, 6: 171 (30 pages).

\* cited by examiner

METHODS TO TREAT NEURODEGENERATIVE DISEASES

CROSS-REFERENCE TO RELATED APPLICATIONS

This application is a continuation of U.S. application Ser. No. 14/420,245, filed on Feb. 6, 2015, which is a 371 U.S. National Application of PCT/US2013/053766, filed on Aug. 6, 2013, which claims priority under 35 U.S.C. § 119(e) to U.S. Provisional Patent Application Nos. 61/680,662, filed on Aug. 7, 2012, and 61/791,055, filed on Mar. 15, 2013, the entire contents of which are hereby incorporated by reference in their entireties.

TECHNICAL FIELD

The claimed methods and compositions relate to methods to treat neurodegenerative diseases.

BACKGROUND

Amyotrophic lateral sclerosis (ALS) is a devastating progressive neurodegenerative disease in which 50% of patients die within 30 months of onset. Some 10% of cases are familial, and mutations in copper/zinc ion-binding superoxide dismutase 1 (SOD1), repeat expansions in the C9orf72 gene, and mutations in fused-in-sarcoma (FUS) comprise as many as 75% of them. C9orf72 expansions also account for approximately 15% of sporadic ALS cases. A mouse model overexpressing human mutant SOD1 G93A recapitulates many features of the disease, such as motor neuron degeneration and early death. However, the vast majority of ALS cases are not due to SOD1 mutations, and the relevance of animal model to these sporadic ALS patients remains unclear. Creating human motor neurons via stem cell technology now offers an opportunity to study the properties of human motor neurons derived from ALS patients, and thereby disease pathology, in both familial and sporadic ALS cases as well as to provide a means to screen for drugs that may treat or reduce a risk of developing the disease.

SUMMARY

The present invention is based, in part, on the discovery that motor neurons derived from patients with a neurodegenerative disease, e.g., ALS, Parkinson's Disease, Alzheimer's Disease, epilepsy, or pain, have decreased delayed rectifier potassium current and increased persistent sodium current compared to motor neurons derived from control healthy individuals. The present invention is also based, in part, on the discovery that the class of compounds known as "potassium channel openers" can be used to treat neurodegenerative diseases, including ALS, Parkinson's Disease, Alzheimer's Disease, epilepsy, and pain.

Accordingly, in one aspect, the present specification provides methods of treating or reducing a risk of developing a neurodegenerative disease, e.g., ALS, e.g., familial ALS or sporadic ALS, Parkinson's Disease, Alzheimer's Disease, epilepsy, or pain, in a subject. The methods can include administering to the subject a therapeutically effective amount of a potassium channel opener, thereby treating or reducing the risk of developing the neurodegenerative disease in the subject. In some embodiments, the potassium channel opener is a KCNQ/Kv7 channel opener, e.g., retigabine, e.g., a halogenated and/or a fluorinated derivative of retigabine, meclofenamic acid, diclofenac, and BMS-204352. In some embodiments, the potassium channel opener is a $K_{ATP}$ channel opener, e.g., diazoxide, minoxidil, nicorandil, pinacidil, and levcromakalim. In some embodiments, the potassium channel opener is a G protein-coupled inwardly-rectifying potassium channel opener, e.g., flupirtine. In some embodiments, the potassium channel opener is a voltage-gated $Ca^{2+}$-activated potassium channel opener or an inward rectifier potassium channel opener. In some embodiments, the methods can further include administering to the subject an anti-neurodegenerative therapy, e.g., riluzole.

Also provided herein are methods of identifying a candidate compound to treat neurodegenerative diseases, e.g., ALS, Parkinson's Disease, Alzheimer's Disease, epilepsy, and pain. The methods can include providing a motor neuron from a subject with a neurodegenerative disease, e.g., a neurodegenerative disease characterized by hyperexcitable neurons; contacting the motor neuron with a test compound, e.g., polypeptides, small molecules, ribonucleic acids, and deoxyribonucleic acids; determining a level of activity of the motor neuron; comparing the level of activity of the motor neuron in the presence of the test compound with a level of activity of the motor neuron in the absence of the test compound; and selecting, identifying, purifying, or isolating the test compound as a candidate compound if there is a lower level of activity of the motor neuron in the presence of the test compound than in its absence. In one embodiment, the methods can include determining whether the candidate compound reduces a symptom of ALS in an animal model, e.g., a mouse model overexpressing human mutant SOD1 G93A, wherein a candidate compound that reduces a symptom of ALS is a candidate compound to treat ALS.

In one embodiment, the motor neuron is obtained from or derived from a subject with a neurodegenerative disease, e.g., ALS, e.g., familial ALS or sporadic ALS, Parkinson's Disease, Alzheimer's Disease, epilepsy, or pain. Determining a level of activity of the motor neuron can include measuring an action potential of the motor neuron, e.g., using patch clamp recording or extracellular multi-electrode array recording. In one embodiment, the methods include determining whether the candidate compound increases survival of the motor neuron.

In another aspect, methods of diagnosing a neurodegenerative disease, e.g., ALS, e.g., familial ALS or sporadic ALS, Parkinson's Disease, Alzheimer's Disease, epilepsy, or pain, are described. The methods can include providing a motor neuron from a subject; determining a level of activity of the motor neuron; comparing the level of activity of the motor neuron with a reference level of activity of a motor neuron; and diagnosing the subject with a neurodegenerative disease if the level of activity of the motor neuron is higher than the reference level of activity.

In one embodiment, the motor neuron is derived from a subject with ALS, e.g., familial ALS or sporadic ALS, Parkinson's Disease, Alzheimer's Disease, epilepsy, or pain. In one embodiment, the methods can include measuring an action potential of the motor neuron, e.g., using patch clamp recording or extracellular multi-electrode array recording. In one embodiment, the method can include administering to a subject diagnosed as having a neurodegenerative disease a therapeutically effective amount of a potassium channel opener, thereby treating the neurodegenerative disease in the subject.

In yet another embodiment, methods of identifying a subject at increased risk of developing a neurodegenerative disease, e.g., ALS, e.g., familial ALS or sporadic ALS, Parkinson's Disease, Alzheimer's Disease, epilepsy, or pain, are provided. The methods can include providing a motor neuron from a subject; determining a level of activity of the motor neuron; comparing the level of activity of the motor neuron with a reference level of activity of a motor neuron; and identifying the subject at increased risk of developing a neurodegenerative disease if the level of activity of the motor neuron is higher than the reference level of activity. In one embodiment, the motor neuron is derived from the subject.

In one embodiment, the methods can include measuring an action potential of the motor neuron, e.g., using patch clamp recording or extracellular multi-electrode array recording. In one embodiment, the method can include administering to a subject identified as at increased risk of developing a neurodegenerative disease a therapeutically effective amount of a potassium channel opener, thereby reducing the risk of developing the neurodegenerative disease in the subject.

In one embodiment, the compound or pharmaceutical composition is administered to the subject orally, intravenously, intrathecally, intraperitoneally, intramuscularly, or by implantation. In another embodiment, the methods further include administering to the subject an anti-neurodegenerative therapy, e.g., riluzole.

The present disclosure also features methods of treating, or reducing a risk of developing, a neurodegenerative disease, e.g., ALS, e.g., familial ALS or sporadic ALS, Parkinson's Disease, Alzheimer's Disease, epilepsy, or pain, in a subject. The methods include providing a somatic cell-derived motor neuron from a subject. In some embodiments, the motor neuron can be derived from a somatic cell, e.g., a fibroblast, lymphocyte, or keratinocyte, by reprogramming an induced pluripotent stem cell to differentiate into a functional motor neuron. In some embodiments, the somatic cell can be directly reprogrammed into a functional motor neuron. The methods include determining a level of activity of the somatic cell-derived motor neuron and comparing the level of activity of the motor neuron with a reference level of activity of a motor neuron. The subject is identified as having, or at increased risk of developing, a neurodegenerative disease if the level of activity of the motor neuron is higher than the reference level of activity. The methods include administering to the subject identified as having or at increased risk of developing a neurodegenerative disease a therapeutically effective amount of a potassium channel opener, thereby treating or reducing the risk of developing the neurodegenerative disease in the subject. In some embodiments, the potassium channel opener is a KCNQ/Kv7 channel opener, a $K_{ATP}$ channel opener, a G protein-coupled inwardly-rectifying potassium channel opener, a voltage-gated $Ca^{2+}$-activated potassium channel opener, or an inward rectifier potassium channel opener. In some embodiments, the potassium channel opener is retigabine, e.g., a halogenated and/or a fluorinated derivative of retigabine, meclofenamic acid, diclofenac, BMS-204352, diazoxide, minoxidil, nicorandil, pinacidil, levcromakalim, or flupirtine. In some embodiments, the methods also include administering to the subject an anti-neurodegenerative therapy, e.g., riluzole.

In the methods described herein, the subject is an animal, human or non-human, and rodent or non-rodent. For example, the subject can be any mammal, e.g., a human, other primate, pig, rodent such as mouse or rat, rabbit, guinea pig, hamster, cow, horse, cat, dog, sheep or goat, or a non-mammal such as a bird.

As used herein, treating or reducing a risk of developing a neurodegenerative disease in a subject means to ameliorate at least one symptom of neurodegenerative disease. In one aspect, the invention features methods of treating, e.g., reducing severity or progression of, a neurodegenerative disease in a subject. The term treating can also include reducing the risk of developing a neurodegenerative disease in a subject, delaying the onset of symptoms of a neurodegenerative disease in a subject, or increasing the longevity of a subject having a neurodegenerative disease. The methods can include selecting a subject on the basis that they have, or are at risk of developing, a neurodegenerative disease, but do not yet have a neurodegenerative disease, or a subject with an underlying neurodegenerative disease. Selection of a subject can include detecting symptoms of a neurodegenerative disease, a blood test, clinical electrophysiological recordings, or imaging tests of the brain. If the results of the test(s) indicate that the subject has a neurodegenerative disease, the methods also include administering a therapeutically effective amount of a potassium channel opener, and detecting an effect of the potassium channel opener in the subject, thereby treating or reducing the risk of developing a neurodegenerative disease in the subject.

As used herein, the term "neurodegenerative disease" refers to a condition having a pathophysiological component of neuronal death. Neurodegeneration is the umbrella term for the progressive loss of structure or function of neurons, including death of neurons. Exemplary examples of such diseases include, but are not limited to, ALS, e.g., familial ALS or sporadic ALS, Parkinson's Disease, Alzheimer's Disease, epilepsy, and pain. ALS and its symptoms are well-known in the art and are described in further detail below. Subjects can be diagnosed as having a neurodegenerative disease by a health care provider, medical caregiver, physician, nurse, family member, or acquaintance, who recognizes, appreciates, acknowledges, determines, concludes, opines, or decides that the subject has a neurodegenerative disease.

The term "amyotrophic lateral sclerosis" or "ALS" also known as motor neuron disease and also as Lou Gehrig's disease, refers to a disease of the nerve cells in the brain and spinal cord that control voluntary muscle movement. In ALS, neurons waste away or die, and can no longer send messages to muscles. This eventually leads to muscle weakening, twitching, and an inability to move the arms, legs, and body. The condition slowly gets worse. When the muscles in the chest area stop working, it becomes hard or impossible to breathe on one's own. ALS affects approximately five out of every 100,000 people worldwide. A subject may be at risk for developing ALS if the subject has a family member who has a hereditary form of the disease. Smoking and military exposure may be subtle risk factors. Symptoms usually do not develop until after age 50, but they can start in younger people. Persons with ALS have a loss of muscle strength and coordination that eventually gets worse and makes it impossible to do routine tasks such as going up steps, getting out of a chair, or swallowing. Breathing or swallowing muscles may be the first muscles affected. As the disease gets worse, more muscle groups develop problems. ALS does not affect the senses (sight, smell, taste, hearing, touch). It only rarely affects bladder or bowel function, or a person's ability to think or reason.

Parkinson's Disease occurs when nerve cells in the brain that make dopamine are slowly destroyed. Without dopamine, the nerve cells in that part of the brain cannot properly send messages. This leads to the loss of muscle function. The damage gets worse with time. The term "parkinsonism" refers to any condition that involves the types of movement changes seen in Parkinson's Disease. Parkinsonism may be caused by other disorders (called secondary parkinsonism) or certain medications. Symptoms may be mild at first, and can include: slow blinking, constipation, difficulty swallowing, drooling, problems with balance and walking, muscle aches and pains, rigid or stiff muscles, and shaking (tremors).

Alzheimer's Disease is a type of dementia that causes problems with memory, thinking and behavior. Symptoms usually develop slowly and get worse over time, becoming severe enough to interfere with daily tasks. Alzheimer's Disease is the most common form of dementia, a general term for memory loss and other intellectual abilities serious enough to interfere with daily life. Alzheimer's Disease accounts for 50 to 80% of dementia cases. Alzheimer's Disease is a progressive disease, where dementia symptoms gradually worsen over a number of years. In its early stages, memory loss is mild, but with late-stage Alzheimer's Disease, individuals lose the ability to carry on a conversation and respond to their environment. Alzheimer's Disease is the sixth leading cause of death in the United States. Those with Alzheimer's Disease live an average of eight years after their symptoms become noticeable to others, but survival can range from four to 20 years, depending on age and other health conditions. Alzheimer's has no current cure, but treatments for symptoms are available and research continues. Although current Alzheimer's Disease treatments cannot stop Alzheimer's Disease from progressing, they can temporarily slow the worsening of dementia symptoms and improve quality of life for those with Alzheimer's Disease and their caregivers. Today, there is a worldwide effort under way to find better ways to treat the disease, delay its onset, and prevent it from developing.

Epilepsy is a common and diverse set of chronic neurological disorders characterized by seizures. Seizures may be recurrent and unprovoked, combined with brain alterations which increase the chance of future seizures. In many cases a cause cannot be identified; however, brain trauma, strokes, brain cancer, and drug and alcohol misuse appear to be involved. Epileptic seizures result from abnormal, excessive, or hypersynchronous neuronal activity in the brain. About 50 million people worldwide have epilepsy, and nearly 80% of epilepsy occurs in developing countries. Epilepsy becomes more common as people age. Onset of new cases occurs most frequently in infants and the elderly. Symptoms vary from person to person. Some people may have simple staring spells, while others have violent shaking and loss of alertness. The type of seizure depends on the part of the brain affected and cause of epilepsy. Most of the time, the seizure is similar to the previous one. Some people with epilepsy have a strange sensation (such as tingling, smelling an odor that isn't actually there, or emotional changes) before each seizure. Epilepsy is usually controlled, but not cured, with medication. However, more than 30% of people with epilepsy do not have seizure control even with the best available medications. Surgery may be considered in difficult cases.

By the phrase "risk of developing disease" is meant the relative probability that a subject will develop a neurodegenerative disease in the future as compared to a control subject or population (e.g., a healthy subject or population).

The term "potassium channel opener" is used to describe a type of compound that facilitates ion transmission through potassium channels. The methods include any potassium channel opener that acts on potassium channels expressed by normal or diseased neurons including motor neurons. These could be determined by mRNA expression profiling and/or electrophysiological experiments. Examples include, but are not limited to KCNQ/Kv7 channel openers, e.g., retigabine, e.g., a halogenated and/or a fluorinated derivative of retigabine, meclofenamic acid, diclofenac, and BMS-204352; $K_{ATP}$ channel openers, e.g., diazoxide, minoxidil, nicorandil, pinacidil, and levcromakalim; G protein-coupled inwardly-rectifying potassium channel openers, e.g., flupirtine; a voltage-gated $Ca^{2+}$-activated potassium channel opener; or an inward rectifier potassium channel opener.

The term "inhibitory RNA" is meant to include a nucleic acid molecule that contains a sequence that is complementary to a target nucleic acid (e.g., a target microRNA or target inflammatory marker) that mediates a decrease in the level or activity of the target nucleic acid. Non-limiting examples of inhibitory RNAs include interfering RNA, shRNA, siRNA, ribozymes, antagomirs, and antisense oligonucleotides. Methods of making inhibitory RNAs are described herein. Additional methods of making inhibitory RNAs are known in the art.

As used herein, "an interfering RNA" refers to any double stranded or single stranded RNA sequence, capable—either directly or indirectly (i.e., upon conversion) of inhibiting or down-regulating gene expression by mediating RNA interference. Interfering RNA includes, but is not limited to, small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family. As used herein, the phrase "post-transcriptional processing" refers to mRNA processing that occurs after transcription and is mediated, for example, by the enzymes Dicer and/or Drosha.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long.

As used herein, an "antagomir" refers to a small synthetic RNA having complementarity to a specific microRNA target, optionally with either mispairing at the cleavage site or one or more base modifications to inhibit cleavage.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DETAILED DESCRIPTION

Figure 1:
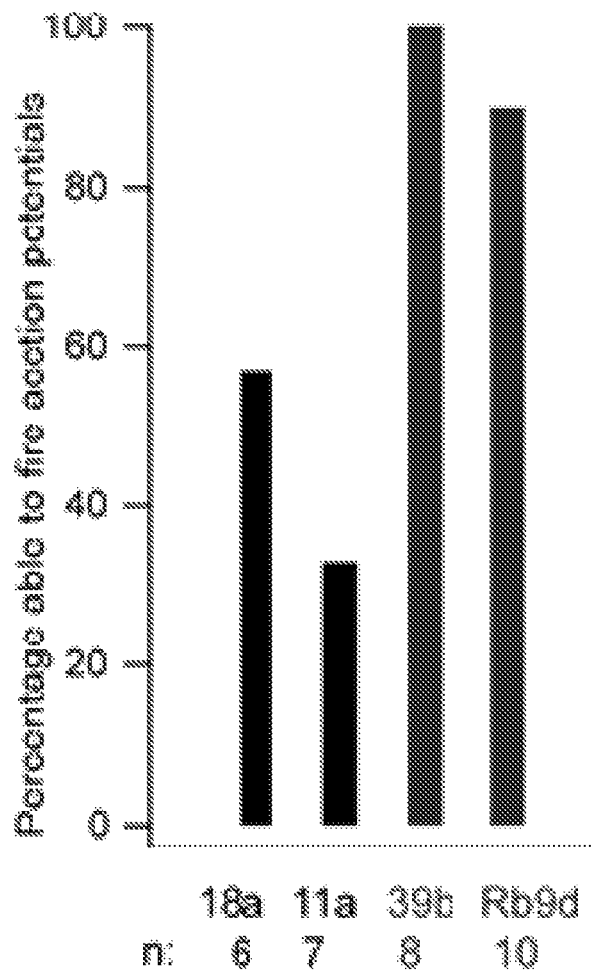
FIG. 1 is a bar graph showing percentage of motor neurons able to fire action potentials from control (18a and 11a) and ALS (39b and Rb9d) patient-derived motor neurons.

The invention described herein is based in part on identification of decreased delayed rectifier potassium current and increased persistent sodium current in motor neurons derived from patients with a neurodegenerative disease, e.g., ALS, e.g., familial ALS or sporadic ALS, Parkinson's Disease, Alzheimer's Disease, epilepsy, or pain, compared to controls. The present methods can be used to treat or reduce a risk of developing a neurodegenerative disease, including ALS, e.g., familial ALS or sporadic ALS, Parkinson's Disease, Alzheimer's Disease, epilepsy, or pain.

Methods of Treating or Reducing a Risk of Developing a Neurodegenerative Disease Provided herein are methods of treating or reducing a risk of developing a neurodegenerative disease (e.g., ALS, e.g., familial ALS or sporadic ALS, Parkinson's Disease, Alzheimer's Disease, epilepsy, or pain) that include administering to a subject a therapeutically effective amount of a potassium channel opener, e.g., retigabine, e.g., a halogenated and/or a fluorinated derivative of retigabine. The methods can involve diagnosing a subject, and administering, e.g., orally, to a subject, having or at risk for developing a neurodegenerative disease, a therapeutically effective amount of a potassium channel opener, e.g., retigabine, e.g., a halogenated and/or a fluorinated derivative of retigabine. The subject can be further monitored for treatment response.

Also featured in the present disclosure are methods of treating, or reducing a risk of developing, a neurodegenerative disease, e.g., ALS, e.g., familial ALS or sporadic ALS, Parkinson's Disease, Alzheimer's Disease, epilepsy, or pain, in a subject. The methods include providing a somatic cell-derived motor neuron from a subject. Motor neurons can be derived from, e.g., somatic cells (e.g., fibroblasts, lymphocytes, keratinocytes), from a subject and be reprogrammed to induced pluripotent stem cells (iPSCs), which divide indefinitely in vitro and retain the ability to differentiate into any cell type (Dimos et al., Science 321:1218-21, 2008; and Kiskinis et al., J Clin Invest 120:51-9, 2010, which are hereby incorporated by reference in their entirety). These iPSCs can then be differentiated by an addition of small molecules as described in Boulting et al. (Nat Biotechnol 29:279-86, 2011, which is hereby incorporated by reference in its entirety) to functional motor neurons. Another way to derive motor neurons from a subject with a neurodegenerative disease is by direct reprogramming of somatic cells (e.g., fibroblasts) to functional motor neurons (Son et al., Cell Stem Cell 9:205-18, 2011, which is hereby incorporated by reference in its entirety).

The methods include determining a level of activity of the somatic cell-derived motor neuron and comparing the level of activity of the motor neuron with a reference level of activity of a motor neuron. The subject is identified as having, or at increased risk of developing, a neurodegenerative disease if the level of activity of the motor neuron is higher than the reference level of activity. The methods also include administering to the subject identified as having or at increased risk of developing a neurodegenerative disease a therapeutically effective amount of a potassium channel opener, thereby treating or reducing the risk of developing the neurodegenerative disease in the subject. In some embodiments, the potassium channel opener is a KCNQ/Kv7 channel opener, a $K_{ATP}$ channel opener, a G protein-coupled inwardly-rectifying potassium channel opener, a voltage-gated $Ca^{2+}$-activated potassium channel opener, or an inward rectifier potassium channel opener. In some embodiments, the potassium channel opener is retigabine, e.g., a halogenated and/or a fluorinated derivative of retigabine, meclofenamic acid, diclofenac, BMS-204352, diazoxide, minoxidil, nicorandil, pinacidil, levcromakalim, or flupirtine. In some embodiments, the methods also include administering to the subject an anti-neurodegenerative therapy, e.g., riluzole.

In some embodiments of any of the methods described herein, the subject is suspected of having, is at risk of having, or has a neurodegenerative disease, e.g., ALS, e.g., familial ALS or sporadic ALS, Parkinson's Disease, Alzheimer's Disease, epilepsy, or pain. It is well within the skills of an ordinary practitioner to recognize a subject that has, or is at risk of developing, a neurodegenerative disease.

In all of the methods described herein, appropriate dosages of the potassium channel opener can readily be determined by those of ordinary skill in the art of medicine, e.g., by monitoring the patient for signs of disease amelioration or inhibition, and increasing or decreasing the dosage and/or frequency of treatment as desired. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue, e.g., motor neuron, in order to minimize potential damage to unaffected cells and, thereby, reduce side effects. Appropriate doses can also be determined by amelioration of abnormal excitability in peripheral nerves detected by clinical electrophysiology or electromyography.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount (i.e., an effective dosage) ranges from about 10 to 2000 mg/day, e.g., about 20 to 1800 mg/day, e.g., about 30 to 1600 mg/day, e.g., about 50 to 1500 mg/day, e.g., about 60 to 1200 mg/day, e.g., about 100 to 1000 mg/day, e.g., about 200 mg/day. Optimal dosage levels can be readily determined by a skilled practitioner, such as a physician, e.g., a neurologist. The compound can be administered one time per day, twice per day, one time per week, twice per week, for between about 1 to 52 weeks per year, e.g., between 2 to 50 weeks, about 6 to 40 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a compound can include a single treatment or, preferably, can include a series of treatments.

For example, for retigabine, e.g., a halogenated and/or a fluorinated derivative of retigabine, an effective amount ranges from about 100 mg/day 200 mg/day, about 400 mg/day, about 500 mg/day, about 600 mg/day, about 800 mg/day, about 900 mg/day, about 1000 mg/day, and about 2000 mg/day.

A subject can be treated (e.g., periodically administered the agent) for a prolonged period of time (e.g., at least one month, two months, six months, one year, two years, three years, four years, five years, or ten years). As described in detail herein, the dosage of the potassium channel opener to be administered to the subject can be determined by a physician by consideration of a number of physiological factors including, but not limited to, the sex of the subject, the weight of the subject, the age of the subject, and the presence of other medical conditions. The potassium channel opener can be administered to the subject orally, intravenously, intrathecally, intraperitoneally, intramuscularly, or by implantation with appropriate change in dosage to reach desired EC50 levels.

The subjects can also be those undergoing any of a variety of additional anti-neurodegenerative therapy treatments. Thus, for example, subjects can be those being treated with riluzole.

Neurodegenerative Diseases

Neurodegenerative diseases are a class of neurological diseases that are characterized by the progressive loss of the structure and function of neurons and neuronal cell death. Inflammation has been implicated for a role in several neurodegenerative diseases. Progressive loss of motor and sensory neurons and the ability of the mind to refer sensory information to an external object is affected in different kinds of neurodegenerative diseases. Non-limiting examples of neurodegenerative diseases include ALS, e.g., familial ALS or sporadic ALS, Parkinson's Disease, Alzheimer's Disease, epilepsy, or pain.

A health care professional may diagnose a subject as having a neurodegenerative disease by the assessment of one or more symptoms of a neurodegenerative disease in the subject. Non-limiting symptoms of a neurodegenerative disease in a subject include difficulty lifting the front part of the foot and toes; weakness in arms, legs, feet, or ankles; hand weakness or clumsiness; slurring of speech; difficulty swallowing; muscle cramps; twitching in arms, shoulders, and tongue; difficulty chewing; difficulty breathing; muscle paralysis; partial or complete loss of vision; double vision; tingling or pain in parts of body; electric shock sensations that occur with head movements; tremor; unsteady gait; fatigue; dizziness; loss of memory; disorientation; misinterpretation of spatial relationships; difficulty reading or writing; difficulty concentrating and thinking; difficulty making judgments and decisions; difficulty planning and performing familiar tasks; depression; anxiety; social withdrawal; mood swings; irritability; aggressiveness; changes in sleeping habits; wandering; dementia; loss of automatic movements; impaired posture and balance; rigid muscles; bradykinesia; slow or abnormal eye movements; involuntary jerking or writhing movements (chorea); involuntary, sustained contracture of muscles (dystonia); lack of flexibility; lack of impulse control; and changes in appetite. A health care professional may also base a diagnosis, in part, on the subject's family history of a neurodegenerative disease. A health care professional may diagnose a subject as having a neurodegenerative disease upon presentation of a subject to a health care facility (e.g., a clinic or a hospital). In some instances, a health care professional may diagnose a subject as having a neurodegenerative disease while the subject is admitted in an assisted care facility. Typically, a physician diagnoses a neurodegenerative disease in a subject after the presentation of one or more symptoms.

Methods for Identifying Compounds to Treat Neurodegenerative Diseases

The present disclosure also provides methods for identifying compounds, e.g., small organic or inorganic molecules (e.g., molecules having a molecular weight less than 1,000 Da), oligopeptides, oligonucleotides, or carbohydrates, capable of reducing motor neuron activity and, therefore, treating neurodegenerative diseases.

Libraries of Test Compounds

In certain embodiments, screens of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids), amino acids, amino acid analogs, polynucleotides, polynucleotide analogs, nucleotides, nucleotide analogs, inhibitory RNAs, shRNAs, small interfering RNAs, antagomirs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res*. (1996) 29:114; Armstrong, R. W.; Combs, A. P.; Tempest, P. A.; Brown, S. D.; Keating, T. A. *Acc. Chem. Res*. (1996) 29:123; Ellman, J. A. *Acc. Chem. Res*. (1996) 29:132; Gordon, E. M.; Gallop, M. A.; Patel, D. V. *Acc. Chem. Res*. (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116: 2661; U.S. Pat. Nos. 5,359,115, 5,362,899, and 5,288,514; PCT Publication Nos. WO92/10092, WO93/09668, WO91/07087, WO93/20242, and WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis," 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. USA* 90:6909 (1993)). Other synthesis methods, including the "tea-bag" technique of Houghten (see, e.g., Houghten et al., *Nature* 354:84-86, 1991) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J Med. Chem.*, supra). Compound libraries can be screened by providing a motor neuron from a subject with a neurodegenerative disease, e.g., a motor neuron derived from a subject with ALS, e.g., familial ALS or sporadic ALS, Parkinson's Disease, Alzheimer's Disease, epilepsy, or pain, contacting the motor neuron with a test compound, determining a level of activity of the motor neuron, and comparing the level of activity of the motor neuron in the presence of the test compound with a level of activity of the motor neuron in the absence of the test compound, wherein a lower level of activity of the motor neuron in the presence of the test compound than in its absence indicates that the test compound is a candidate compound to treat ALS, e.g., familial ALS or sporadic ALS, Parkinson's Disease, Alzheimer's Disease, epilepsy, or pain. The level of activity of the motor neuron can be determined by measuring an action potential of the motor neuron, e.g., using patch clamp recording or extracellular multi-electrode array (MEA) recording.

Exemplary assays useful for screening libraries of test compounds are described herein.

Screening Methods

The invention provides methods for identifying compounds capable of modulating motor neuron activity. Although applicants do not intend to be bound by any particular theory as to the biological mechanism involved, such compounds are thought to specifically (1) increase delayed rectifier potassium current and/or (2) decrease persistent sodium current in motor neurons.

In certain aspects of the present invention, screening for such compounds is accomplished by (i) contacting a motor neuron from a subject with ALS, e.g., a motor neuron derived from a subject with ALS with a test compound; determining a level of activity of the motor neuron; and comparing the level of activity of the motor neuron in the presence of the test compound with a level of activity of the motor neuron in the absence of the test compound. Test compounds that lower the level of activity of the motor neuron are referred to herein as "candidate compounds." Candidate compounds can be further tested and found to be capable of reducing in vivo activity of a motor neuron.

As described herein, motor neurons can be derived from a subject with a neurodegenerative disease, e.g., ALS, e.g., familial ALS or sporadic ALS, Parkinson's Disease, Alzheimer's Disease, epilepsy, or pain, by art-known methods. For example, somatic cells (e.g., fibroblasts, lymphocytes, keratinocytes) from a subject with ALS can be reprogrammed to induced pluripotent stem cells (iPSCs), which divide indefinitely in vitro and retain the ability to differentiate into any cell type (Dimos et al., Science 321:1218-21, 2008; Kiskinis et al., J Clin Invest 120:51-9, 2010). These iPSCs can then be differentiated by an addition of small molecules as described in Boulting et al. (Nat Biotechnol 29:279-86, 2011) to functional motor neurons. Another way to derive motor neurons from a subject with ALS is by direct reprogramming of somatic cells (e.g., fibroblasts) to functional motor neurons (Son et al., Cell Stem Cell 9:205-18, 2011).

Motor neuron activity could be assayed in a high-throughput system, recording large numbers (hundreds) of neurons within each well of a multi-well MEA device (such as from Axion systems which can use a 96 well format) or recording individual neurons from a low throughput technique such as patch clamp. As an example of high-throughput usage, motor neuron activity can be recorded in 96 wells pre-filled with individual compounds, different doses of compounds, or a combination of compounds. Assessment of activity may also be made by calcium imaging, which can be used in both low- and high-throughput formats.

In vivo testing of candidate compounds can be performed by means known to those in the art. For example, the candidate compound(s) can be administered to a mammal, such as a rodent (e.g., murine) or rabbit. Such animal model systems are art-accepted for testing potential pharmaceutical agents to determine their therapeutic efficacy in patients, e.g., human patients. Animals that are particularly useful for in vivo testing are wild type animals or non-wild type animals (e.g., mice) that over-produce mutant human SOD1 (SOD1$^{G93A}$). In a typical in vivo assay, an animal (e.g., a wild type or transgenic mouse) is administered, by any route deemed appropriate (e.g., by injection), a dose of a candidate compound. Conventional methods and criteria can then be used to monitor animals for signs of reduction of motor neuron activity. If needed, the results obtained in the presence of the candidate compound can be compared with results in control animals that are not treated with the test compound.

The level of activity of a motor neuron can be determined by measuring an action potential of the motor neuron. Action potentials can be measured by patch clamp recording or extracellular MEA recording. Patch clamp recording is a laboratory technique that allows the study of single or multiple ion channels in cells. The technique can be applied to a wide variety of cells, but is especially useful in the study of excitable cells such as neurons. Patch clamp recording makes it possible to record the currents of single ion channels.

Patch clamp recording uses, as an electrode, a glass micropipette that has an open tip diameter of about one micrometer. The interior of the micropipette is filled with a solution matching the ionic composition of the bath solution, as in the case of cell-attached recording, or the cytoplasm for whole-cell recording. A chlorided silver wire is placed in contact with this solution and conducts electric current to the amplifier. The micropipette is pressed against a cell membrane and suction is applied to assist in the formation of a high resistance seal between the glass and the cell membrane. The high resistance of this seal makes it possible to electronically isolate the currents measured across the membrane patch with little competing noise, as well as providing some mechanical stability to the recording.

Patch clamp recording uses a single electrode to record currents. Many patch clamp amplifiers do not use true voltage clamp circuitry but instead are differential amplifiers that use the bath electrode to set the zero current level. This allows a researcher to keep the voltage constant while observing changes in current. Alternatively, the cell can be current clamped in whole-cell mode, keeping current constant while observing changes in membrane voltage.

Extracellular MEAs are devices that contain multiple plates or shanks through which neural signals are obtained or delivered, essentially serving as neural interfaces that connect neurons to electronic circuitry. When recording, the electrodes on an MEA transduce a change in voltage from the environment carried by ions into currents carried by electrons. The size and shape of a recorded signal depend upon several factors: the nature of the medium in which the cell or cells are located (e.g., the medium's electrical conductivity, capacitance, and homogeneity); the nature of contact between the cells and the MEA electrode (e.g., area of contact and tightness); the nature of the MEA electrode itself (e.g., its geometry, impedance, and noise); the analog signal processing (e.g., the system's gain, bandwidth, and behavior outside of cutoff frequencies); and the data sampling properties (e.g., sampling rate and digital signal processing). For the recording of a single cell that partially covers a planar electrode, the voltage at the contact pad is approximately equal to the voltage of the overlapping region of the cell and electrode multiplied by the ratio the surface area of the overlapping region to the area of the entire electrode.

Drugs detected from their effects on excitability on human motor neurons from subjects with a neurodegenerative disease, e.g., ALS, e.g., familial ALS or sporadic ALS, Parkinson's Disease, Alzheimer's Disease, epilepsy, or pain, can be tested for their effects on motor neuron survival in vitro.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

Diagnostic Methods

Also provided herein are methods of diagnosing a neurodegenerative disease, e.g., ALS, e.g., familial ALS or sporadic ALS, Parkinson's Disease, Alzheimer's Disease, epilepsy, or pain, in a subject by providing a motor neuron from a subject with a neurodegenerative disease, a subject suspected of having a neurodegenerative disease, or a subject at risk for a neurodegenerative disease, and determining a level of activity of the motor neuron. The level of activity of the motor neuron can be compared to a reference level of activity of a motor neuron, e.g., motor neuron activity from a healthy cohort. A subject with a motor neuron with a higher level of activity than a reference level of activity indicates that the subject has a neurodegenerative disease as outlined in detail below.

In some embodiments, a subject can be diagnosed as having ALS, e.g., familial ALS or sporadic ALS, Parkinson's Disease, Alzheimer's Disease, epilepsy, or pain, if the level of activity of a motor neuron from the subject is higher than a reference level of activity. In some embodiments, a subject diagnosed as having a neurodegenerative disease, e.g., ALS, e.g., familial ALS or sporadic ALS, Parkinson's Disease, Alzheimer's Disease, epilepsy, or pain, can be administered a therapeutically effective amount of a potassium channel opener, e.g., KCNQ/Kv7 channel openers, e.g., retigabine, e.g., a halogenated and/or a fluorinated derivative of retigabine, meclofenamic acid, diclofenac, and BMS-204352; $K_{ATP}$ channel openers, e.g., diazoxide, minoxidil, nicorandil, pinacidil, and levcromakalim; G protein-coupled inwardly-rectifying potassium channel openers, e.g., flupirtine; voltage-gated $Ca^{2+}$-activated potassium channel openers; and/or inward rectifier potassium channel openers, thereby treating or reducing the risk of developing the neurodegenerative disease in the subject.

Any of the methods described herein can be performed on subjects presenting to a health care facility (e.g., a hospital, clinic, or an assisted care facility). The subjects may present with one or more symptoms of a neurodegenerative disease (e.g., any of the symptoms of a neurodegenerative disease described herein). The subject can also present with no symptoms (an asymptomatic subject) or just one symptom of a neurodegenerative disease. The subject can have a familial history of a neurodegenerative disease (e.g., familial ALS).

The diagnostic methods described herein can be performed by any health care professional (e.g., a physician, a laboratory technician, a nurse, a physician's assistant, and a nurse's assistant). The diagnostic methods described herein can be used in combination with any additional diagnostic testing methods known in the art (e.g., the observation or assessment of one or more symptoms of a neurodegenerative disease in a subject).

Methods of Identifying a Subject at Risk of Developing a Neurodegenerative Disease Also provided are methods of identifying a subject at risk of developing a neurodegenerative disease, e.g., ALS, e.g., familial ALS or sporadic ALS, Parkinson's Disease, Alzheimer's Disease, epilepsy, or pain. These methods include providing a motor neuron from a subject and determining a level of activity of the motor neuron. The level of activity of the motor neuron can be compared to a reference level of activity of a motor neuron, e.g., motor neuron activity from a healthy cohort. A subject with a motor neuron with a higher level of activity than a reference level of activity indicates that the subject is at risk of developing a neurodegenerative disease.

The subjects may present with one or more symptoms of a neurodegenerative disease (e.g., any of the symptoms of a neurodegenerative disease described herein). The subject can also present with no symptoms or just one symptom of a neurodegenerative disease. The subject can have a family history of a neurodegenerative disease (e.g., familial ALS).

Subjects identified as at risk of developing a neurodegenerative disease may be administered a treatment for a neurodegenerative disease or may be administered a new or alternative treatment for a neurodegenerative disease. Subjects identified as at risk of developing a neurodegenerative disease can also undergo more aggressive therapeutic treatment (e.g., increased periodicity of clinic or hospital visits).

EXAMPLES

The invention is further described in the following examples, which do not limit the scope of the invention described in the claims. The examples involve ALS, although skilled practitioners will appreciate that methods may be applied to other neurodegenerative diseases, e.g., Parkinson's Disease, Alzheimer's Disease, epilepsy, and pain.

Figure 2:
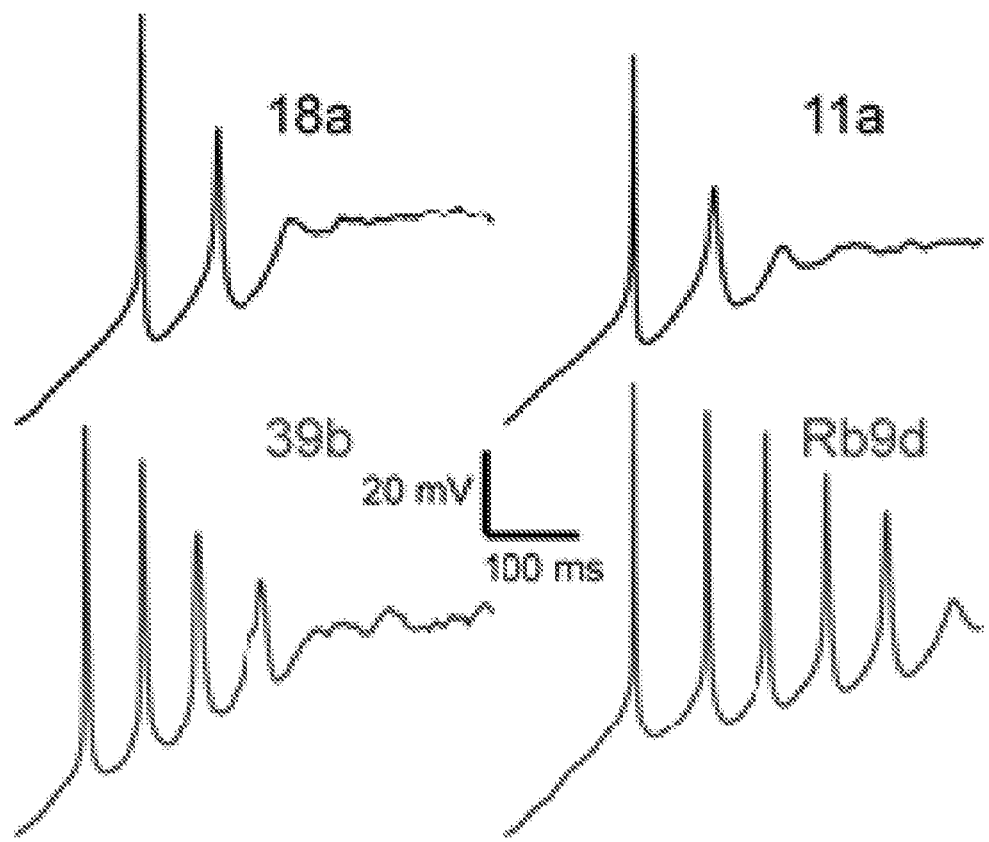
FIG. 2 shows action potentials recordings elicited by ramp depolarizations in control (18a and 11a) and ALS (39b and Rb9d) patient-derived motor neurons.

Example 1: Action Potential Firing Properties of Motor Neurons Derived from Patients with ALS and Age-Matched Control Subjects Experiments were performed using iPS-derived motor neurons from two familial ALS subjects, both of whom harbored the same extremely aggressive $SOD1^{A4V}$ mutation (39b, Rb9d, both with disease onset in the 40s and death within one-two additional years), and two separate age-matched control subjects (11a, 18a). All lines were determined to be karyotypically normal, and all were efficient in motor neuron differentiation (~50%). Using two separate techniques, patch clamp and extracellular MEA recording, an increased excitability of motor neurons derived from familial ALS patients compared to controls was found (FIG. 1). During ramp depolarizations in current clamp, the number of action potentials fired by ALS motor neurons was larger than in control motor neurons (p<0.05, Mann-Whitney U test) (FIG. 2). Input resistance, capacitance, and resting membrane potential were not different among the groups, suggesting that these findings were not related to, for example, poor health of the familial ALS-derived motor neurons. These results were obtained in experiments from three separate differentiations, arguing against a result of a poor differentiation of a particular line.

Figure 3:
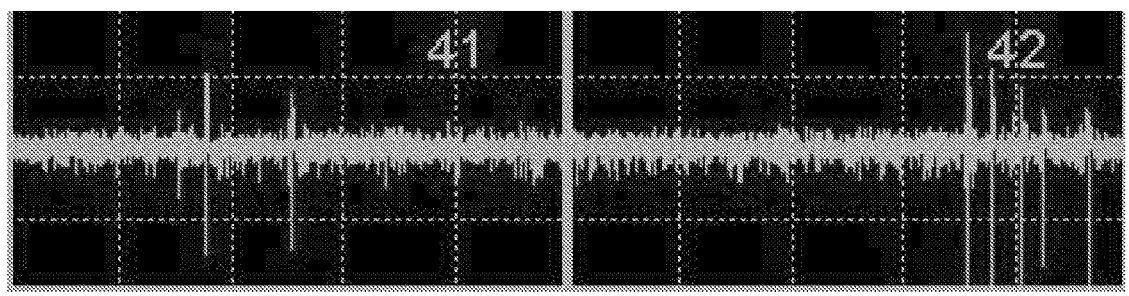
FIG. 3 is plot of spontaneous action potentials in extracellular MEA recording from two of 64 electrodes.
Figure 4:
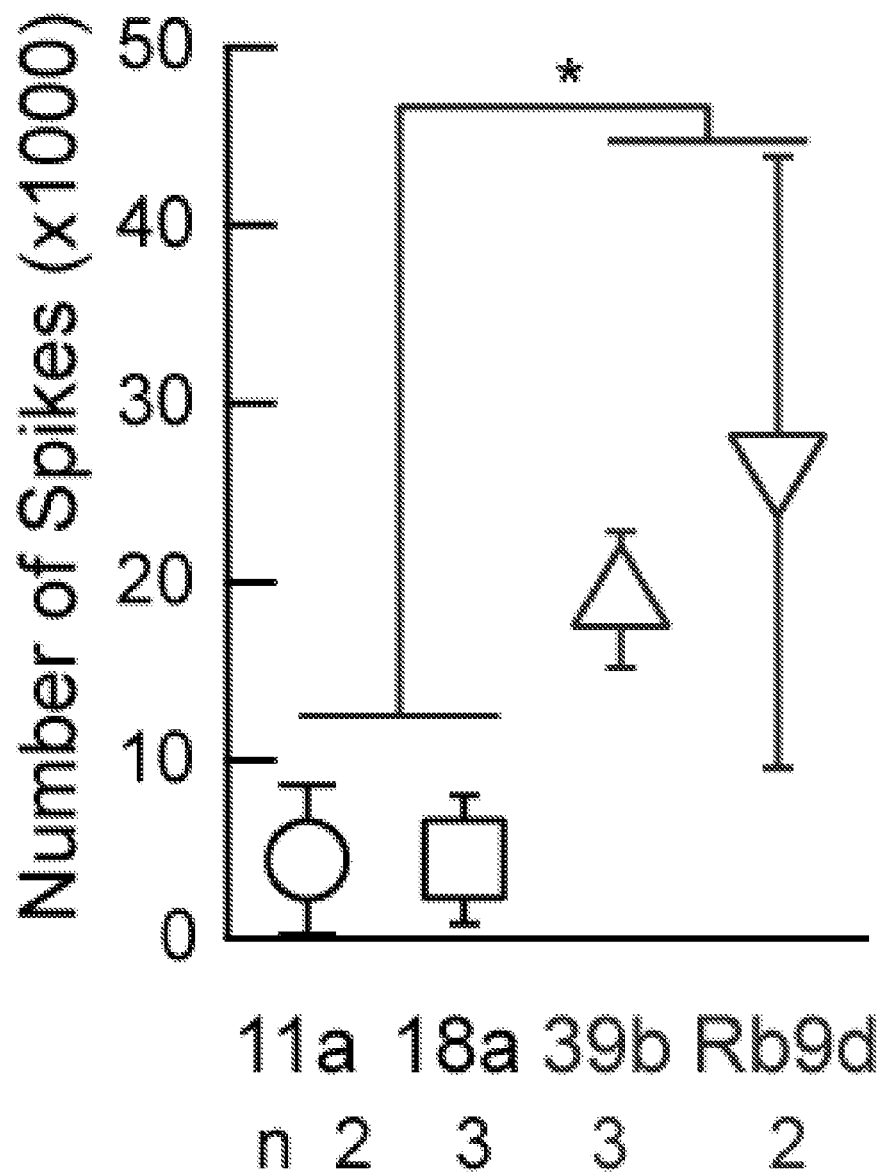
FIG. 4 is a graph of number of spikes in one minute of MEA recording.
Figure 5:
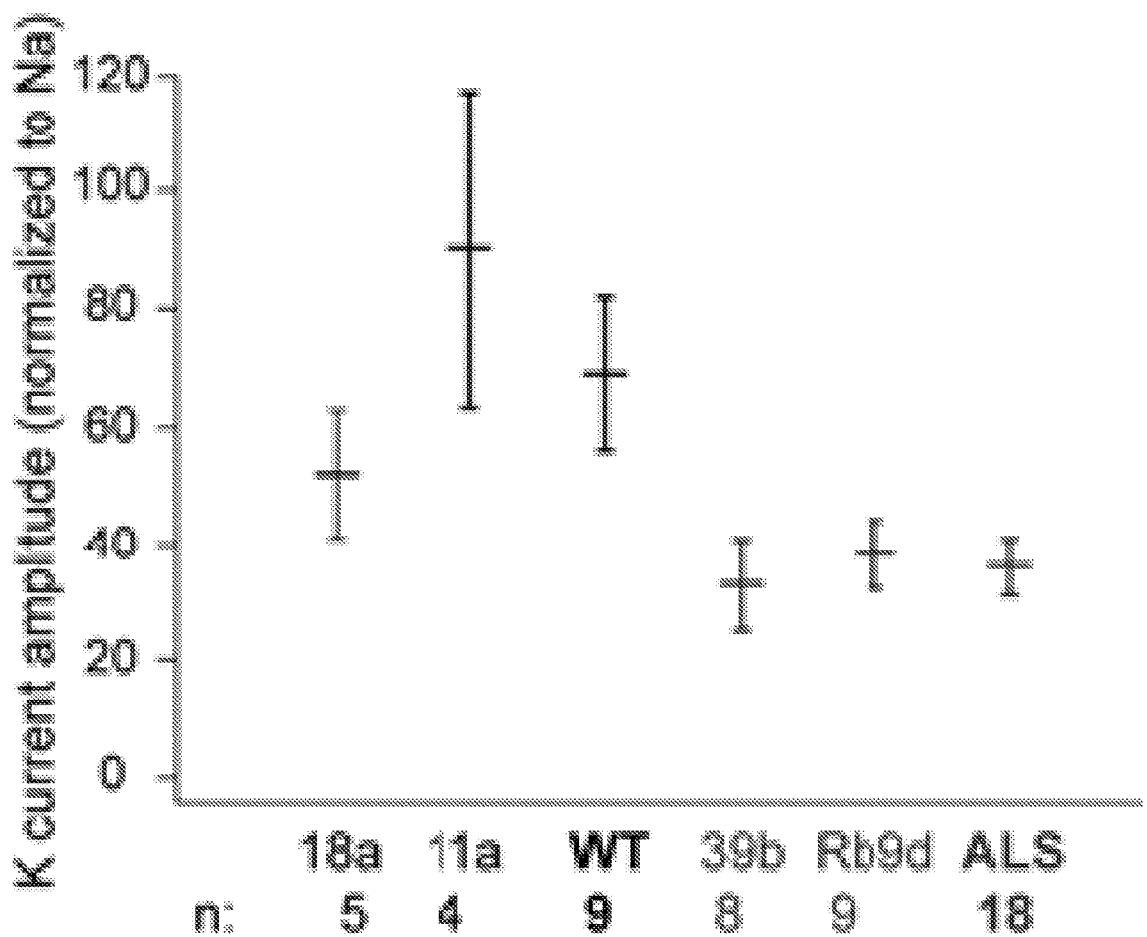
FIG. 5 is a series of bar graphs depicting firing rate in one minute of MEA recording.

Because patch clamp experiments can only evaluate relatively small numbers of cells, extracellular MEA recording was used to evaluate spontaneous firing in large numbers of neurons, and a robust increase in the number of spontaneous action potentials in familial ALS-derived motor neurons was found (FIGS. 3-4, p<0.05 Mann-Whitney U test, and experimental details below). A 2-3 fold increase in the number of spontaneously firing neurons in the familial ALS-derived neurons compared to control-derived neurons was observed; moreover, a larger number of mutant neurons than controls fired at fast frequencies (FIG. 5), thus accounting for the large difference in spike number. Similar results have been obtained in two to three separate motor neuron differentiations.

Motor neurons from two aggressive familial ALS lines and two controls have been evaluated. Patch clamp will be used to evaluate motor neurons from two additional aggressive SOD1 familial ALS cases (two early onset G85S patients, four total), four sporadic ALS cases (screened for known familial ALS mutations, four total), and two additional controls (four total). A large number of karyotypically normal iPSC lines from sporadic ALS, familial ALS, and controls (nearly 100 disease and control subjects, and growing) are available, as well as extensive experience in differentiating the lines into motor neurons (Boulting et al., Nat Biotechnol 2011: 29, 279-86). Accompanying each ALS line is information regarding patient age of onset, an indicator of disease severity. Differentiation protocol is based on dual-SMAD inhibition (Chambers et al., Nat Biotechnol 2009: 27, 275-80) and modification of the original morphogen-based approach (Wichterle et al., Cell 2002: 110, 385-97). An equal number of disease and control lines will be differentiated into motor neurons at each time in order to control as much as possible for variation in differentiation efficiency. Data from each cell line will be pooled from at least three separate differentiations. All recordings will take place at approximately four weeks in culture, as at this time point well-developed motor neuron electrical activity and substantial numbers of surviving motor neurons have been observed in culture.

Figure 6:
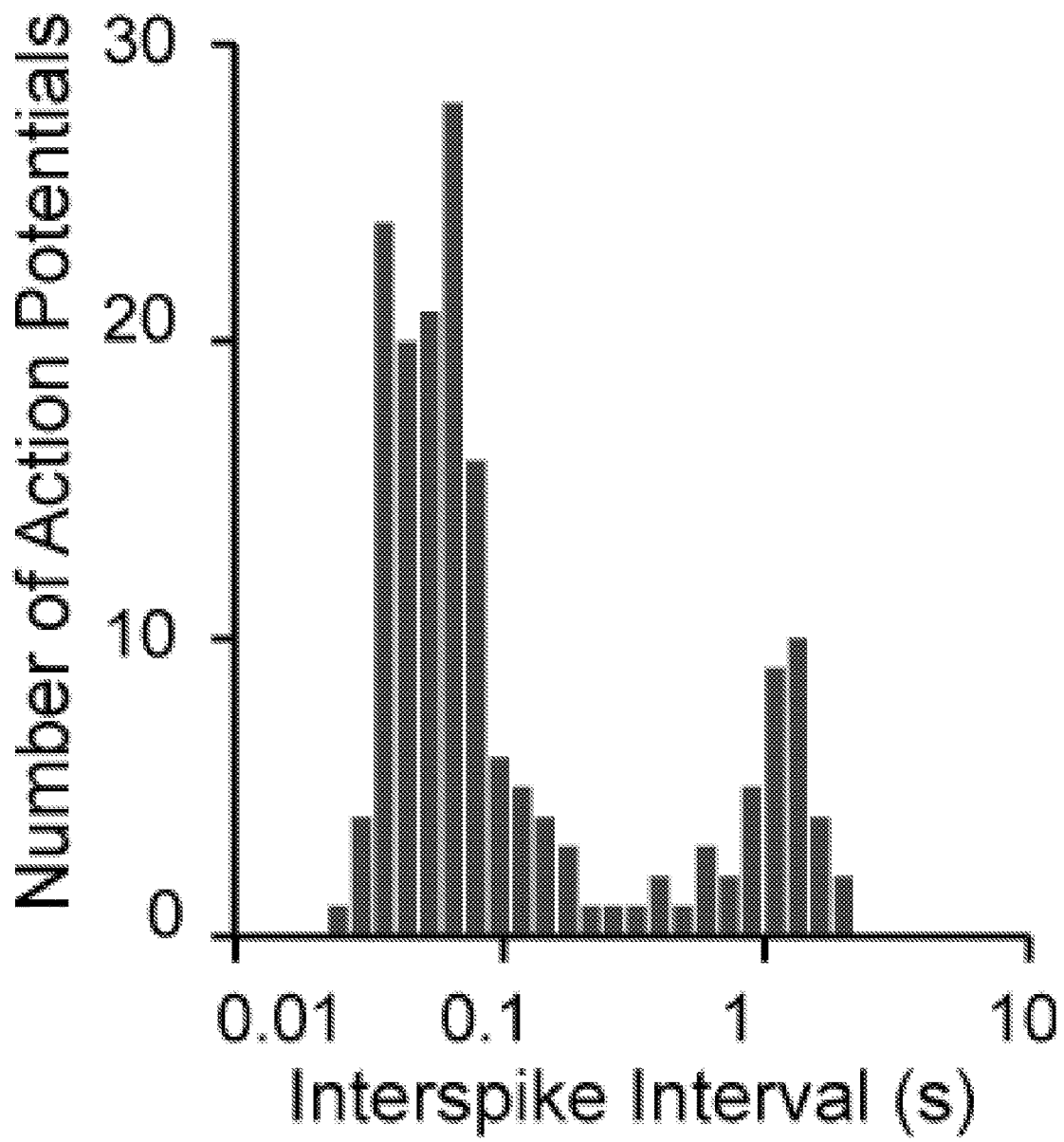
FIG. 6 is a histogram of interspike interval from a single bursting ALS-derived neuron in one minute of MEA recording

Extracellular recordings will be performed using a MED64 MEA amplifier to record from an 8×8 array of extracellular electrodes (Alpha Med Scientific) after plating equal numbers of cells on each array. Because each action potential has a distinct morphology, spike-clustering software can be used to determine the number of spontaneously firing neurons (Lewicki, Network 1998: 9, R53-78; Cohen et al., Nat Neurosci 2011: 14, 811-9). Custom Matlab programs have been written to ensure that neurons whose spikes are detected by multiple electrodes are only counted once. Average spiking frequency for each neuron and individual interspike intervals (ISI) between consecutive spikes of each neuron will be calculated. A non-bursting neuron should have a distribution of ISIs described by a single Poisson distribution, while a bursting neuron will have a bimodal distribution of ISIs (or log of ISI), as shown in FIG. 6. Individual bursting and non-bursting neurons will be identified based on deviation from Poisson fits of ISIs for particular neurons (Bastian et al., Journal of Neurophysiology 2001: 85, 10-22) and the number and percentage of bursting neurons will be quantified.

Figure 7:
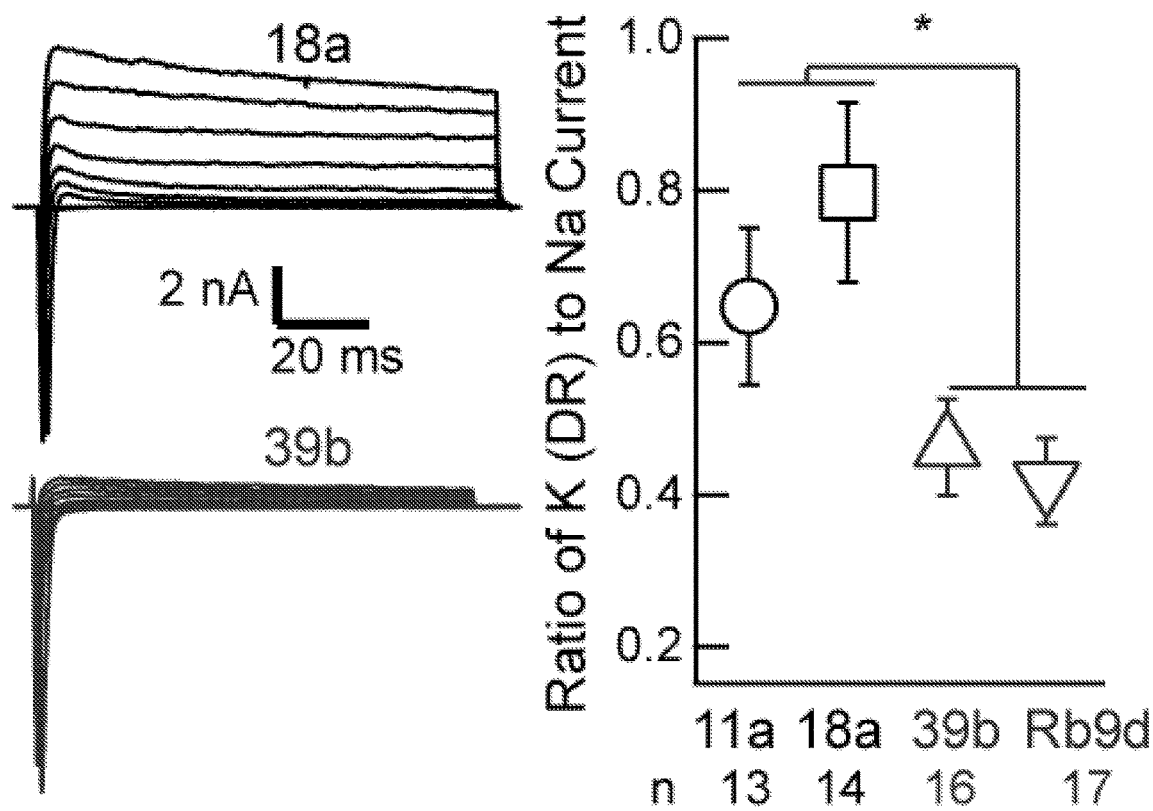
FIG. 7 shows delayed rectifier potassium current amplitudes (relative to peak sodium current) in control (18a and 11a) and ALS (39b and Rb9d) patient-derived motor neurons ($p<0.05$).

Example 2: Phenotype the Major Classes of Ion Channels and Receptors Present in iPSC-Derived Motor Neurons and Determine Whether Reducing Channel Activity Improves Motor Neuron Survival In Vitro In repeated differentiations of motor neurons from the two control and two SOD1$^{A4V}$ iPSC lines, the relative amplitude of the steady-state delayed rectifier potassium current was markedly smaller in disease compared to control motor neurons. The relative amplitudes were quantified, and a significant decrease was found between control and familial ALS-derived motor neurons (FIG. 7, $p<0.05$, t-test).

Figure 8:
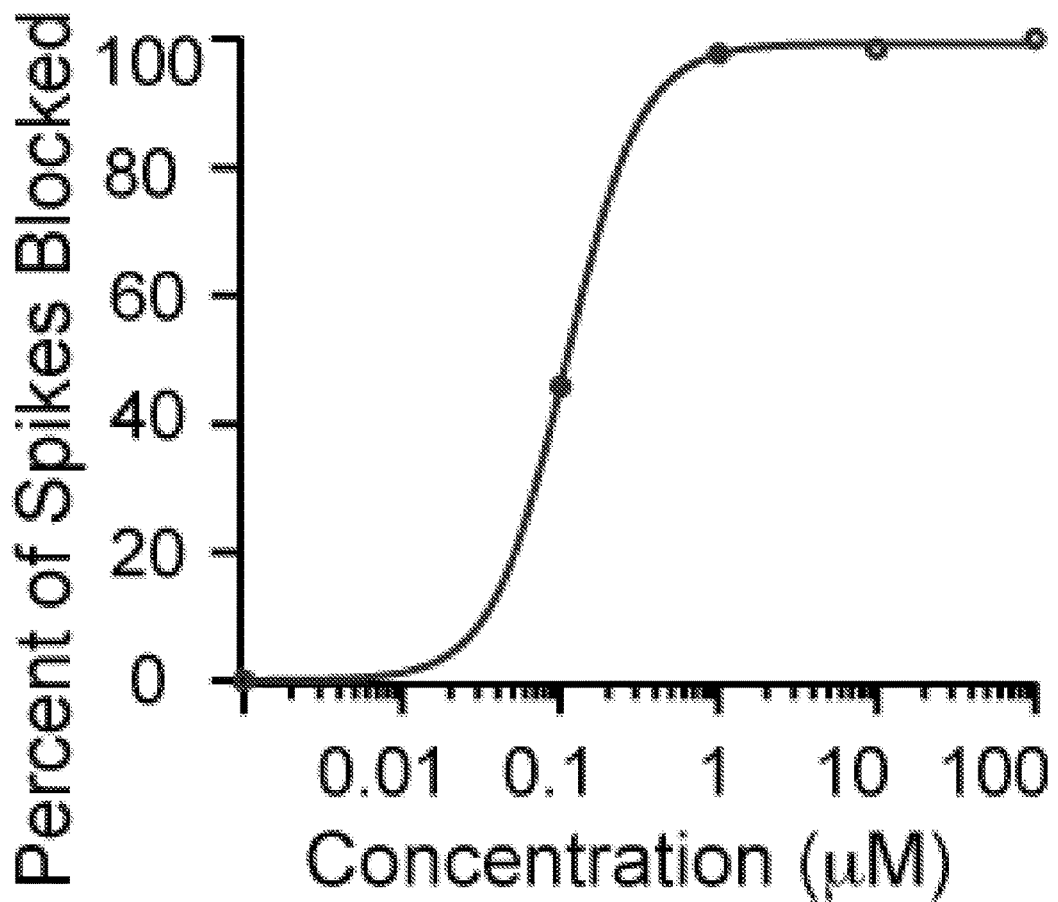
FIG. 8 is a Hill plot of block of spontaneous action potentials by retigabine in ALS patient-derived motor neurons (39b).

Retigabine, an FDA-approved activator of Kv7 currents (although at higher concentrations, it may potentiate GABA responses), suppressed spontaneous firing as assessed by MEA recording at 100 nM, a concentration thought to be physiologically relevant to its pharmacological activity in patients and similar to its documented EC50 on Kv7 channels (Ferron et al., Br J Clin Pharmacol 2003: 56, 39-45; Wickenden et al., Mol Pharmacol 2000: 58, 591-600) (FIG. 8). While the Hill plot was from a single MEA (~300 active neurons), 100% were blocked with 10 µM on two additional MEAs from separate differentiations. In addition, RT-PCR data from the neurons show high Kv7 mRNA levels.

Figure 9:
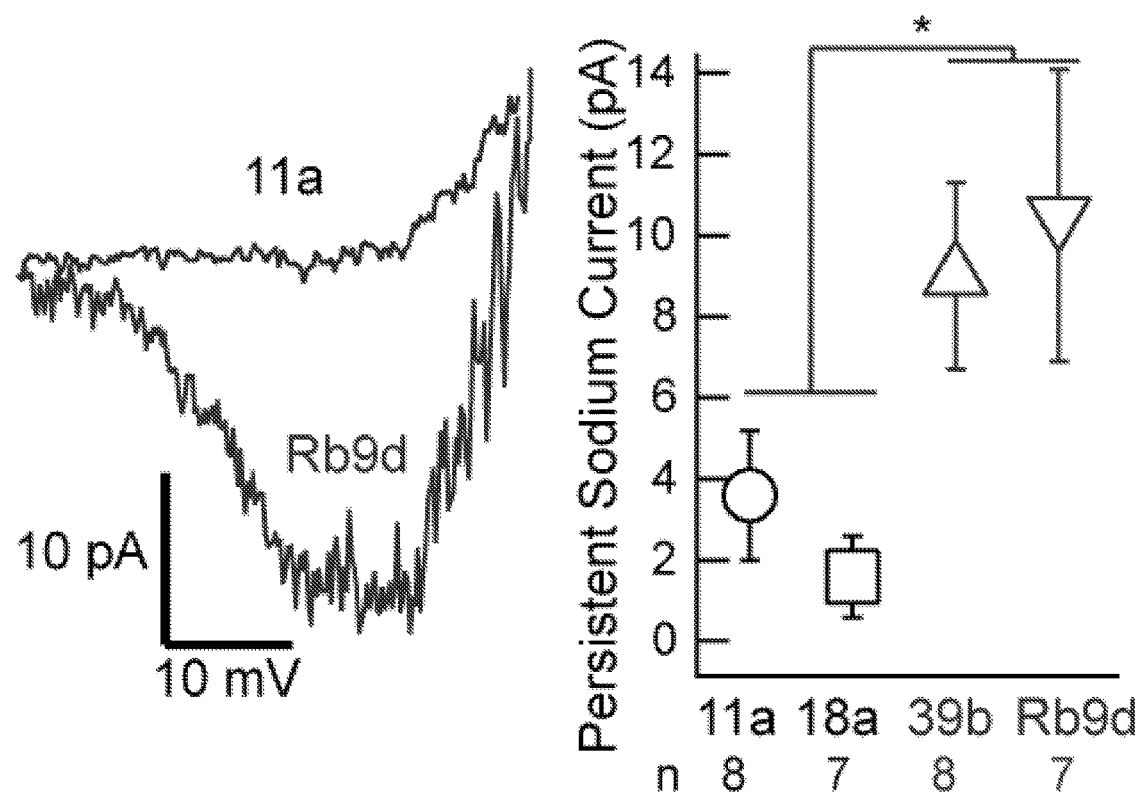
FIG. 9 depicts persistent sodium current plotted as a function of voltage during slow ramp depolarization in control (18a and 11a) compared to ALS (39b and Rb9d) patient-derived motor neurons (*$p<0.01$).

Small persistent sodium currents that were larger in ALS-derived motor neurons than controls have been measured (FIG. 9, $p<0.05$, t-test). This finding was not due to differences in cell size, as the capacitance measurements were not different between the groups. While these currents are small, the fact that the persistent sodium current does not inactivate means that it still can potentially have a potent effect on neuronal firing.

Experiments have been performed in which no difference in amplitudes of responses to the excitatory neurotransmitter kainate or to the inhibitory neurotransmitters GABA and glycine have been observed.

Example 3: Test Retigabine and Other Test Compounds in the SOD1$^{G93A}$ Mouse Model Retigabine and other test compounds will be tested to determine whether they delay disease onset or reduce mortality in SOD1$^{G93A}$ mice. Other tests will also be used to detect improved motor function, force, reduced motor neuron or ventral root loss, maintained innervation, or preserved muscle mass, all of which are affected in SOD1$^{G93A}$ mice. Gurney et al., Science 1994: 264, 1772-5; Fischer et al., Exp Neurol 2004: 185, 232-40; and Mead et al., PLoS ONE 2011: 6, e23244). The onset of disease in SOD1G93A mice is classically reported around 90 days of age, and death usually occurs at 130-140 days. Crude signs of disease onset typically involve tremor in one limb. However, rotarod performance has been found to decline several weeks before such manifestations.

Because the mice have been used extensively in drug studies, there are consensus guidelines for conducting studies and reliable estimates of the numbers needed to obtain statistically meaningful results (Ludolph et al., Amyotroph Lateral Scler 2010: 11, 38-45; and Mead et al., PLoS ONE 2011: 6, e23244). 15 animals per group will allow detection of a 20% improvement in rotarod performance, a value thought to be biologically relevant and a sensitive indicator of disease onset, with 80% power at a significance level of 0.05. Additional outcomes require 5-7 animals per group to obtain biologically relevant improvements with 80% power and significance level 0.05. 60 four week-old high copy number SOD1$^{G93A}$ transgenic mice (Jackson 002726) will be divided randomly into two groups, one to receive active drug and the second to receive vehicle. Each group of 30 mice will randomly be divided into two again, 15 animals for behavior/survival and 15 for histology, with full blinding for all experiments and analysis. Equal numbers of males and females will be maintained for all comparisons. Transgene copy numbers will be checked only if reduction is suspected by phenotype (Mead et al., PLoS ONE 2011: 6, e23244).

Retigabine has recently been used in mice treated with doses from 1-10 mg/kg given via intraperitoneal (IP) injection, and studies of the drug in epilepsy models have documented CSF uptake (mass spectrometry of spinal cord could be used if necessary). In a study evaluating retigabine to treat peripheral neuropathy, mice were treated with 10 mg/kg IP injection for several weeks without apparent side effects (Nodera et al., Neuroscience Letters 2011: 505, 223-7). We will treat mice with IP injection of vehicle or 10 mg/kg retigabine five days per week from age four weeks until death.

Analyses for histological and behavioral tests are performed using t-tests between groups with appropriate correction for multiple comparisons. Disease onset and survival curves are analyzed by Kaplan Meir and Logrank Mantel-Cox tests, respectively. Five mice in each group are sacrificed for histological experiments at each time point of 60, 90, and 120 days (30 mice total). Motor neuron quantification, neuromuscular junction (NMJ) analysis, ventral root counts, and muscle weights are performed with these five mice/group. For motor neuron quantification, Image J software is used to detect NeuN-stained lumbar ventral-horn neurons with area >450 µm², a standard criteria for motor neurons. For NMJ analysis, the gastrocnemius muscles are excised, weighed, and co-stained sections with antibodies to neurofilament 200 and labeled alpha-bungarotoxin. NMJs are identified based on bungarotoxin staining and pretzel-shaped morphology, and the number of NMJs are counted, as well as the number of innervated NMJs based on overlap of bungarotoxin and neurofilament signals. The number of NMJs, percent innervated and percent denervated are quantified. For ventral root counts, thin sections are stained with toluidine blue, large and small fiber axons counted with Image J software, and the absolute number and percentage of small and large fiber axons are quantified. The second 30 mice are used for behavioral and survival studies (n=15 in each group). Mice behavior is analyzed starting at 40 days of age and tests performed biweekly. Animal weight is recorded. Maximum muscle force is measured musing grip strength analysis and motor function using an accelerating rotarod. These behavioral tests are commonly used and will be performed in triplicate.

Effects of retigabine on wild-type littermates in both behavior and histology will be controlled for using five animals per group for behavior and five for histology analyzed at 120 days only (10 treated, 10 untreated).

Figure 10:
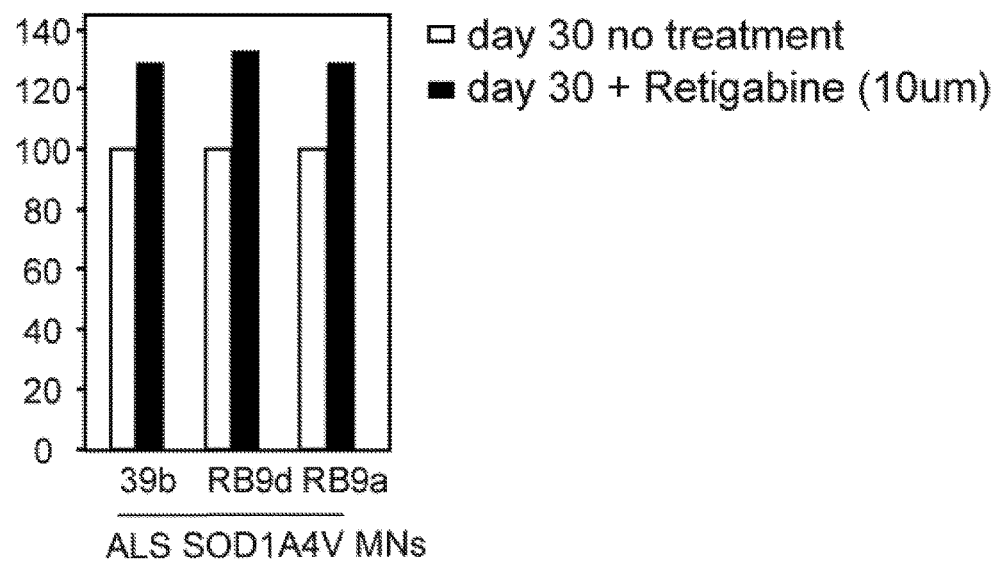
FIG. 10 is a bar graph showing that retigabine increased survival of motor neurons derived from ALS subjects.

Example 4: Retigabine Increased Survival of Motor Neurons Derived from ALS Subjects ALS patient-derived motor neurons were identified by positive stain for ISL and TUJ1 after 30 days in culture with or without retigabine (10 µM). The drug increased the survival of the motor neurons (FIG. 10).

Figure 11:
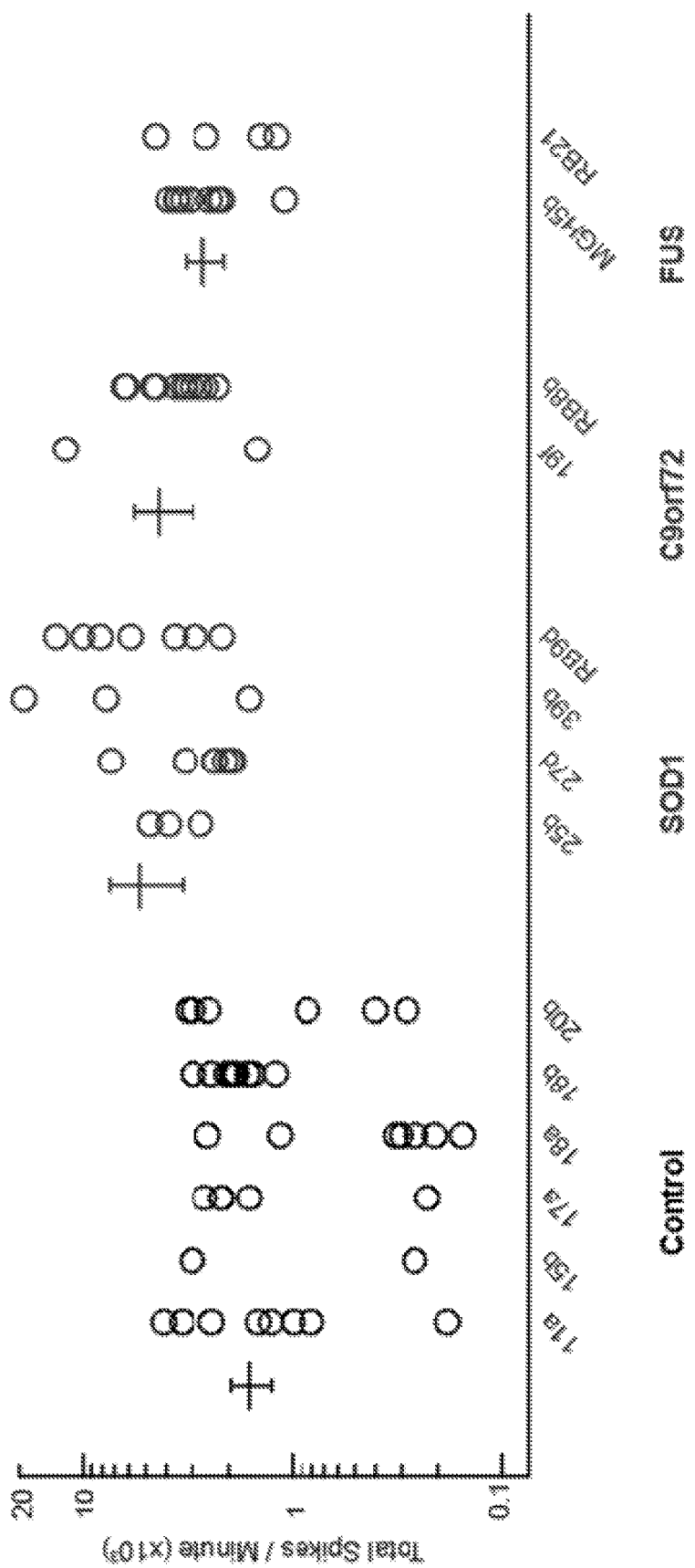
FIG. 11 is a graph of number of spikes in one minute of MEA recording of motor neurons from four control patients (five lines), four SOD1 patients, two C9orf72 repeat expansions, and two FUS patients.
Figure 12:
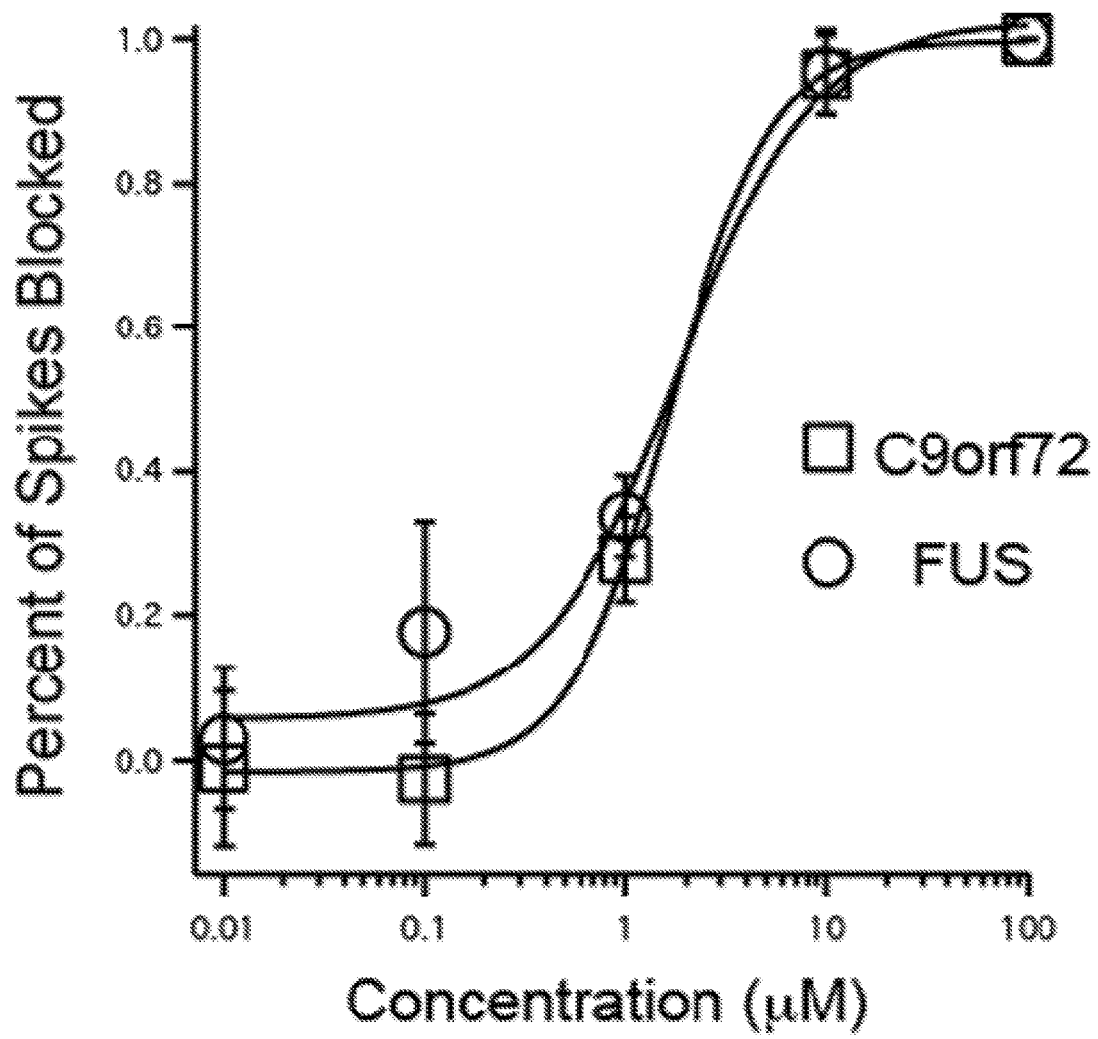
FIG. 12 is a Hill plot of block of spontaneous action potentials by retigabine in C9orf72- and FUS-derived motor neurons.

Example 5: Retigabine Increased Survival of Motor Neurons Derived from ALS Subjects SOD1-derived motor neurons (four lines from four individual unrelated subjects), C9orf72-derived motor neurons (two lines from two individual unrelated subjects), FUS-derived motor neurons (four lines from two individual unrelated subjects) were hyperexcitable compared to motor neurons derived from seven iPSC lines made from five individual healthy controls (FIG. 11). Retigabine blocks the firing of the C9orf72 and FUS-derived motor neurons (FIG. 12). iPSC line and motor neuron generation for these experiments were performed exactly as for the previously studied $SOD1^{A4V}$ and control lines. All lines were karyotypically normal, and all were efficient in motor neuron differentiation. 25b contains a $SOD1^{D90A}$ mutation; 27d contains a $SOD1^{G85S}$ mutation; MGH5b contains a frameshift mutation at FUS residue 1529; and RB21 contains a H517Q FUS mutation. Both 19f and RB8B iPSC lines were generated from patient fibroblasts that carry an extended number of repeat expansions in the gene C9orf72. All iPSCs are generated via 3-factor (OCT4/SOX2/KLF4) retroviral reprogramming as previously described in Dimos et al. (Science 321:1218-21, 2008); and Boulting et al. (Nat Biotechnol 29:279-86, 2011). Line RB8B was generated by 4-factor reprogramming (OCT4/SOX2/KLF4/cMYC) in the same manner. All lines have been quality controlled for pluripotency using standard assays, including staining for NANOG and the Scorecard analysis as described in Bock et al. (Cell 144:439-452, 2011). Control lines 11a, 15b, 17a, 18a, 18b and 20b have previously been published in Boulting et al. (Nat Biotechnol 29:279-86, 2011).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or reducing a risk of developing amyotrophic lateral sclerosis (ALS) in a subject, the method comprising administering to the subject a therapeutically effective amount of a potassium channel opener, thereby treating or reducing the risk of developing ALS in the subject.

2. The method of claim 1, wherein the ALS is familial ALS.

3. The method of claim 1, wherein the potassium channel opener is a KCNQ/Kv7 channel opener, a $K_{ATP}$ channel opener, a G protein-coupled inwardly-rectifying potassium channel opener, a voltage-gated $Ca^{2+}$-activated potassium channel opener, or an inward rectifier potassium channel opener.

4. The method of claim 1, wherein the potassium channel opener is retigabine, a halogenated derivative of retigabine, a fluorinated derivative of retigabine, meclofenamic acid, diclofenac, BMS-204352, diazoxide, minoxidil, nicorandil, pinacidil, levcromakalim, or flupirtine.

5. The method of claim 1, wherein the potassium channel opener is retigabine.

6. The method of claim 1, the method further comprising administering to the subject an anti-neurodegenerative therapy.

7. The method of claim 6, wherein the anti-neurodegenerative therapy is riluzole.

8. The method of claim 1, wherein the subject has a mutation in superoxide dismutase 1 (SOD1).

9. The method of claim 8, wherein the mutation is $SOD1^{A4V}$.

10. The method of claim 1, wherein the ALS is sporadic ALS.

11. The method of claim 1, wherein the subject is a human subject.

* * * * *